United States Patent [19]

Narayanan et al.

[11] Patent Number: 5,227,509
[45] Date of Patent: Jul. 13, 1993

[54] PROCESS FOR MANUFACTURE OF ORGANIC ESTERS OF STRONG ACIDS

[75] Inventors: Kolazi S. Narayanan, Palisades Park; Paul D. Taylor, West Milford, both of N.J.

[73] Assignee: ISP Investments Inc., Wilmington, Del.

[21] Appl. No.: 520,042

[22] Filed: May 7, 1990

[51] Int. Cl.$^5$ .............................. C07C 331/00
[52] U.S. Cl. ........................ 558/10; 558/11; 558/13; 558/15
[58] Field of Search .............. 558/10, 11, 13, 15

[56] References Cited

U.S. PATENT DOCUMENTS

| | | | |
|---|---|---|---|
| 3,014,058 | 12/1961 | Willard et al. | 260/46 |
| 3,306,810 | 2/1967 | Buckman et al. | 162/161 |
| 3,524,871 | 8/1970 | Matt | 260/454 |
| 3,524,872 | 8/1970 | Matt | 260/454 |
| 4,087,451 | 5/1978 | Merianos | 260/454 |
| 4,880,894 | 11/1989 | Sunkel et al. | 558/10 |

FOREIGN PATENT DOCUMENTS 2118160A 10/1983 United Kingdom .................. 558/10

OTHER PUBLICATIONS

Standard Methods for the Examination of Water and Wastewater, 1985, 16th Edition, APHA, AWWA, WPCF–pp. 348–350.
Mechanism and Theory in Organic Chemistry, Thomas Lowry and Kathleen Richardson, Harper & Row, Publishers, New York, etc., pp. 165–168 and pp. 374–375 (1972).
Noller, "Chemistry of Organic Compounds", pp. 118 & 861, W. B. Soundus Co., Philadelphia, 1965.

*Primary Examiner*—David B. Springer
*Attorney, Agent, or Firm*—Jules E. Goldberg; Marilyn J. Maue; Joshua J. Ward

[57] ABSTRACT

A method for preparing $(R)X_{m-p}A_p$ by reacting $(R)X_m$ and MA in N-methylpyrrolidone and recovering the by-product MX as a precipitate wherein:

X is halide;

R contains from 1 to 8 carbon atoms, can be substituted or unsubstituted, and is straight or branched chain alkyl, cycloaliphatic, aralkyl, alkylene, alkenyl, alkenylene, alkynyl or alkynylene with the proviso that X is not attached to a carbon atom having a double bond;

$A^-$ is a monovalent anion soft base selected from the group consisting of halide different from X, $SCN^-$, $SH^-$, $SO_3H^-$, $R_2PO_4^-$, $PF_6^-$, and $[SP(Z)(OR^1)_2]^-$ wherein $R^1$ is lower alkyl and z i sulfur or oxygen;

M is an alkali metal or $NH_4^+$;

m is an integer from 1 to 3 with the proviso that m is 1 or 2 when R has one carton; and P is an integer from 1 to m.

13 Claims, No Drawings

PROCESS FOR MANUFACTURE OF ORGANIC ESTERS OF STRONG ACIDS

BACKGROUND OF THE INVENTION

It is known to produce compounds having the formula $(R)X_{m-p}A_p$ (hereinafter Compound III) as defined below by the reaction sequence:

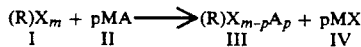

$$\underset{I}{(R)X_m} + \underset{II}{pMA} \longrightarrow \underset{III}{(R)X_{m-p}A_p} + \underset{IV}{pMX}$$

wherein:

X is halide;

R contains from 1 to 8 carbon atoms, can be substituted or unsubstituted, and is straight or branched chain alkyl, cycloaliphatic, aralkyl, alkylene, alkenyl, alkenylene, alkynyl or alkynylene with the proviso that X is not attached to a carbon atom having a double bond;

$A^-$ is a monovalent anion soft base selected from the group consisting of halide other than X, $3CN^-$, $SH^-$, $SO_2H^-$, $R_2PO_4$, $R_2PO_3^-$, $PF_6^-$, and $[SP(Z)(OR^1)_2]^-$ wherein $R^1$ is lower alkyl and Z is sulfur or oxygen;

M is an alkali metal or $NH_4^+$;

m is an integer from 1 to 3 with the proviso that m is 1 or 2 when R has one carbon; and p is an integer from 1 to m.

As used herein, a soft base means an anion of a relatively large size and having a diffused charge. See: (1) Pearson, R. G., Survey of Progress in Chemistry, 5 (1969, Academic Press); (2) Lowry, T. H., and Richardson, K. S., Mechanism and Theory in Organic Chemistry, Harper & Row, New York, NY (1976) pp. 165-168; 374-375. Soft bases having the formulas $SCN^-$ and $[SP(Z)(OR^1)_2]^-$ are disclosed in U.S. Pat. Nos. 4,087,451, and 3,014,058, respectively. As used herein, lower alkyl means an alkyl having from 1 to 4 carbon atoms.

The R group may be substituted with halide, nitro, cyano, and other conventional substituents which do not interfere with the reaction.

Typical of such compounds is methylene bisthiocyanate which is well-known for use limiting the growth and reproduction of microorganisms. It is particularly of use in the paper industry to prevent the growth of fungi, bacteria, and other microorganisms or enzymes produced by the growth. (See, U.S. Pat. No. 3,306,810.)

Traditionally, this reaction has been carried out in aqueous solvent although other solvents, such as cyclic aromatics have been used. (See, U.S. Pat. 3,524,871 and British Published Patent Application 2,118,160a.)

A major problem with the prior art process is that the by-product metal halide MX, e.g., sodium bromide, is left in the mother liquor. This is a waste material since the compound $(R)X_{m-p}A_p$ precipitates out and is formulated in a separate step from the synthesis. For example, when compound III is methylene bisthiocyanate prepared from $CH_2Br_2$ or sodium or ammonium thiocyanate, the mother liquor, after separation of the $(R)X_{m-p}A_p$ contains about 45% of the metal halide, about 3% of the reactant MA, and from 0.5-1% of the $(R)X_{m-p}A_p$. This is a hazardous waste material. The $(R)X_{m-p}A_p$ which is precipitated is then treated in an aqueous dispersion or a nonaqueous solvent, such as, dimethyl formamide, alcohols, and the like. The aqueous dispersion is undesirable because of its great instability resulting from sudden changes in temperature. It is desirable that it be maintained as a homogeneous solution for use.

SUMMARY OF THE INVENTION

We have discovered a method for the one-step preparation of Compound III which facilitates the handling of the by-product metal halide and provides the product in an immediately usable form without further formulation or treatment. More particularly, we have discovered that by reacting a halide of formula I and a metal compound of formula II in N-methylpyrrolidone, the reaction proceeds relatively rapidly to completion and the by-product metal halide precipitates from the solution. The product, Compound III, remains dissolved in the reaction solution. Because of the compatibility of N-methylpyrrolidone with environmental systems, the Compound III in solution may be used directly without further treatment. Moreover, the metal halide by-product is easily separated by precipitation and filtration and can be re-used.

DETAILED DESCRIPTION OF THE INVENTION

The process of the present invention is carried out by mixing N-methylpyrrolidone with Compounds I and II at a temperature and for a period of time sufficient to complete the reaction. The completion of the reaction is evidenced by the disappearance of one of the reactants. Thereafter, the reaction mixture is cooled and filtered to remove precipitated metal halide. The filtrate may be used as is and typically, would contain concentrations of Compound III in the range from about 5 to 25% by weight. Conversions are in the range from about 70 to 90%, based on the weight of starting halide (Compound I). The recovery of the metal halide is generally in the range from about 80 to 90%. Of course, additional conventional surface active agents or other adjuvants can be added to the reaction solution.

The present process is advantageous inasmuch as a separate formulation step is not required and the expensive metal halide is recovered. Also, no water is required for the reaction and there is no need to displace any aqueous halide salt. This results in improved economics for the process. In addition, we have found that the reaction can be carried out at relatively low temperatures in the range from about 40° to 60° C. Preferably, the reaction is carried out at about 50° C. The time period for the reaction to go to completion can be from about 20 minutes to 24 hours depending on the temperature. The higher the temperature, the more rapid the reaction. The preferred time period is from about 20 minutes to 6 hours.

The reactants are normally added in essentially a stoichiometric ratio of about 1 mole of Compound I to 1 to 3 moles of Compound II. A ten to twenty percent excess of the materials may be used.

A catalyst is not needed since the solvent appears to have a catalytic effect. Normally, the amount of the N-methylpyrrolidone used is from about 1 to 5 times the weight of the reactants. Preferably, the amount of solvent used is equivalent to the combined weight of the alkyl dihalide and thiocyanate salt.

The following example illustrates the invention:

EXAMPLE 1

A four-necked 500 ml round-bottom flask was fitted with a magnetic stirrer, thermometer, two water condensers, and a nitrogen gas inlet and outlet. It was charged with 50.63 grams of NaSCN (0.63 moles) and 100 grams of N-methyl-2-pyrrolidone (1 mole). The mixture formed a pasty slurry and its temperature increased to about 50° C. 45.15 grams (0.26 moles) of methylene dibromide was admixed to the slurry over a period of twenty minutes while the reaction mixture was maintained under nitrogen gas at about 53° C. The reaction mixture maintained at this temperature for an additional 24 hours. After this time, practically all of the methylene dibromide had reacted as determined by gas chromatography.

A white precipitate settled to the bottom of the flask and this was separated by suction filtration. The precipitate was sodium bromide. The amount of sodium bromide produced and gas chromatography analysis of the filtrate confirmed that the yield of methylene dithiocyanate was 83%.

A portion of the filtrate (28 grams) was used to isolate the product. This was achieved by adding water slowly to the filtrate. When six grams of water had been added, the methylene thiocyanate began to precipitate. After 35 grams of water had been added, the product was completely precipitated from solution. This product was separated and dried. It weighed 5.0 grams and melted at 102°-104° C. Gas chromatography of the purified product in N-methylpyrrolidone showed 1 peak other than the solvent peak. $^1H_{nmr}$ and $^{13}C_{nmr}$ and infrared spectra were identical with that of a known pure sample of methylene bisthiocyanate. The product yield based on the total recovered methylene bisthiocyanate was 73%. The estimated purity of the product was 99+%. This cyanate was determined spectrophotometrically. See "Standard Methods" for the Examination of Water and Waste Water, 16th Ed. (1985); American Assoc. of Public Health, American Water Works Assoc.; Water Pollution Control Federation; Editors; Greenberg, A.E., et al - pages 348-350.

EXAMPLE 2

The same procedure of Example 1 was used. A reaction flask was charged with 16.40 grams of NaSCN (0.203 mole), 18.82 grams of $CH_2Br_2$ (0.108 mole) and 100 grams N-methyl-2-pyrrolidone. The temperature rose to 39° C. from an initial 25° C. upon addition of the reagents. It took one hour for all the solids to dissolve while stirring with a mechanical stirrer. After a period of 72 hours standing at room temperature under $N_2$ with mild stirring, analysis of the reaction mixture showed 38% reaction completion of the reaction via $^-SCN$ consumption as well as isolation of methylene bisthiocyanate from an aliquot of the reaction mixture.

EXAMPLE 3

Example 2 was repeated using 16.17 grams (0.1996 mole) of NaSCN, 17.50 grams of $CH_2Br_2$ (0.1006 mole) and 99.6 grams of N-methylpyrrolidone. The temperature was maintained at 54° to 62° C. for a period of 5 hours. Analysis of the reaction mixture via GC analysis showed 8% of the total $CH_2Br_2$ remained and a yield of 61% of methylene bisthiocyanate. The $^-SCN$ consumption was monitored by determination of $^-SCN$ spectrophotometrically as described in "Standard Methods" for the Examination of Water and Waste Water, 16th Edition (1985), American Public Health Assoc., American Water Works Assoc., Water Pollution Control Federation, Editors: Greenberg, A. E., et al pages 348-350.

What is claimed is:

1. In a method for the preparation of a compound having the formula $(R)X_{m-p}A_p$ comprising dissolving a compound having the formula $(R)X_m$ and a compound having the formula pMA in a solvent, wherein:

X is halide;

R contains from 1 to 8 carbon atoms, can be substituted or unsubstituted, and is straight or branched chain alkyl, cycloaliphatic or alkynylene with the proviso that X is not attached to a carbon atom having a double bond;

$A^-$ is a monovalent anion soft base selected from the group consisting of halide different from X, $SCN^-$, $SH^-$, $SO_3H^-$, $R_2PO_4$, $R_2PO_4^-$, $PF_6^-$, and $[SP(Z)(OR^1)_2]^-$ wherein $R^1$ is lower alkyl and Z is sulfur or oxygen;

M is an alkali metal or $NH_4^+$;

m is an integer from 1 to 3 with the proviso that m is 1 to 2 when R has one carbon; and p is an integer from 1 to m;

and heating the mixture at a temperature and for a time period sufficient to drive the reaction to conversion, the improvement wherein the solvent consists essentially of N-methylpyrrolidone.

2. The method of claim 1 wherein the temperature is in the range from about 40° to 60° C.

3. The method of claim 1 wherein the temperature is about 50° C.

4. The method of claim 1 wherein the heating is carried out for a time period of from about 20 minutes to 18 hours.

5. The method of claim 1 wherein the heating is carried out for a time period of from about 20 minutes to 6 hours.

6. The method of claim 1 wherein the heating is carried out at a pressure of from about 1 to 51 atmosphere.

7. The method of claim 1 wherein a consolvent selected from the group consisting of N-alkyklpyrrolidone, the alkyl portion of which contains 8 to 16 carbon atoms and a polyol is used.

8. The method of claim 7 wherein the polyol is selected from the group consisting of propylene glycol, polypropylene and polyethylene diol.

9. The method of claim 1 wherein stoichiometric amounts of the compounds having the formula $(R)X_m$ and MA are used.

10. A solution of a compound having the formula $(R)X_{m-p}A_p$ obtained by the method of claim 1.

11. A solution of a compound having the formula $(R)X_{m-p}A_p$ obtained by the method of claim 7.

12. The method of claim 1 wherein (R) $X_{m-p}A_p$ is methylene bisthiocyanate.

13. The method of claim 1 wherein $(R)X_m$ is methylene dibromide and pMA is NaSCN.

* * * * *